(12) United States Patent
Trpkovski (10) Patent No.: US 7,184,146 B2
(45) Date of Patent: Feb. 27, 2007

(54) METHODS AND APPARATUS FOR EVALUATING INSULATING GLASS UNITS

(75) Inventor: Paul Trpkovski, Loganville, WI (US)

(73) Assignee: Cardinal IG Company, Eden Prairie, MN (US)

( * ) Notice: Subject to any disclaimer, the term of this patent is extended or adjusted under 35 U.S.C. 154(b) by 355 days.

(21) Appl. No.: 10/875,640

(22) Filed: Jun. 24, 2004

(65) Prior Publication Data

US 2005/0012926 A1    Jan. 20, 2005

Related U.S. Application Data

(60) Provisional application No. 60/482,127, filed on Jun. 24, 2003.

(51) Int. Cl.
*G01J 3/46* (2006.01)
*G01N 21/62* (2006.01)

(52) U.S. Cl. .............. 356/402; 356/319; 356/437; 156/378

(58) Field of Classification Search .......... 356/239.1, 356/319, 402, 437; 156/378, 379; 65/377, 65/378, 158; 73/23.2
See application file for complete search history.

(56) References Cited

U.S. PATENT DOCUMENTS

| | | |
|---|---|---|
| 3,793,167 A | 2/1974 | Glaser |
| 3,935,351 A | 1/1976 | Franz |
| 4,204,029 A | 5/1980 | Batchelor et al. |
| 4,369,084 A | 1/1983 | Lisec |
| 4,397,533 A | 8/1983 | Naruse et al. |
| 4,402,611 A | 9/1983 | Yuasa |
| 4,476,169 A | 10/1984 | Nishino et al. |
| 4,780,164 A | 10/1988 | Rueckheim et al. |
| 4,848,138 A | 7/1989 | Marshall |
| 4,886,095 A | 12/1989 | Lisec |
| 4,917,495 A | 4/1990 | Steenhoek |
| 4,939,926 A | 7/1990 | Welch |
| 4,995,727 A | 2/1991 | Kawagoe et al. |
| 5,115,668 A | 5/1992 | Welch |
| 5,168,155 A | 12/1992 | Arima et al. |
| 5,198,773 A | 3/1993 | Latta |
| 5,214,494 A | 5/1993 | Inaba et al. |
| 5,303,139 A | 4/1994 | Mark |
| 5,377,473 A | 1/1995 | Narayan et al. |
| 5,432,609 A | 7/1995 | Sugiyama et al. |

(Continued)

FOREIGN PATENT DOCUMENTS

DE    195 21 568 A1    1/1997

OTHER PUBLICATIONS

Gasglass 1002, Leaflet downloaded from www.sparklike.com prior to Sep. 21, 2004.

(Continued)

*Primary Examiner*—Gregory J. Toatley, Jr.
*Assistant Examiner*—Marissa J. Detschel
(74) *Attorney, Agent, or Firm*—Fredrikson & Byron, PA (57) ABSTRACT

An apparatus and method for measuring the color and gas fill concentration of insulating glass units is disclosed. One apparatus includes a color measuring device and gas fill concentration measuring device coupled to a production line for manufacturing insulating glass units. One method of the invention involves measuring the color and gas fill concentration of insulating glass units after they have been filled with gas and sealed.

63 Claims, 9 Drawing Sheets

U.S. PATENT DOCUMENTS

| | | | |
|---|---|---|---|
| 5,439,716 | A | 8/1995 | Larsen |
| 5,567,258 | A | 10/1996 | Lee et al. |
| 5,570,179 | A | 10/1996 | Weckstrom |
| 5,570,192 | A | 10/1996 | Terauchi et al. |
| 5,592,294 | A | 1/1997 | Ota et al. |
| 5,679,419 | A | 10/1997 | Larsen |
| 5,705,010 | A | 1/1998 | Larsen |
| 5,712,592 | A | 1/1998 | Stimson et al. |
| 5,714,214 | A | 2/1998 | Larsen |
| 5,735,318 | A | 4/1998 | Vianello |
| 5,762,739 | A | 6/1998 | Lenhardt et al. |
| 5,831,740 | A | 11/1998 | Terauchi |
| 5,859,709 | A | 1/1999 | Imura |
| 5,920,400 | A | 7/1999 | Eisemann et al. |
| 5,957,169 | A | 9/1999 | Trpkovski |
| 5,963,334 | A | 10/1999 | Yamaguchi et al. |
| 5,978,606 | A | 11/1999 | Ishikawa |
| 6,020,959 | A | 2/2000 | Imura |
| 6,068,720 | A | 5/2000 | McHugh |
| 6,088,177 | A | 7/2000 | Imura et al. |
| 6,158,483 | A | 12/2000 | Trpkovski |
| 6,216,751 | B1 | 4/2001 | Trpkovski |
| 6,462,819 | B1 | 10/2002 | Terauchi et al. |
| 6,538,388 | B2 | 3/2003 | Nakano et al. |
| 6,567,278 | B2 | 5/2003 | Rufer et al. |
| 6,586,887 | B1 | 7/2003 | Oogoshi et al. |
| 6,614,518 | B1 | 9/2003 | Ishikawa et al. |
| 6,707,553 | B1 | 3/2004 | Imura |
| 6,727,654 | B2 | 4/2004 | Ogawa et al. |
| 6,750,614 | B2 | 6/2004 | Nakano et al. |
| 6,795,178 | B1 * | 9/2004 | Rasanen et al. ............ 356/311 |
| 6,926,782 | B2 * | 8/2005 | McGlinchy .................. 156/64 |
| 2004/0266013 | A1 * | 12/2004 | Erickson et al. ............... 436/8 |

OTHER PUBLICATIONS

Gasglass 1002 Instructions Manual downloaded from www.sparklike.com prior to Sep. 21, 2004.

AAMA® Glass Material Council, "Non-destructive Test Device Could Improve IG Quality Control," Newsletter, vol. 2, Issue 2, 8 pgs. (Sep. 2004).

Giard, E., "The I's Have It" US Glass, The Magazine of Influence for Glass Industry Leaders, vol. 37 Issue 1, 7 pgs. (Jan. 2002).

Giard Chilcoat, E., "Dotting All the I's," US Glass, The Magazine of Influence for Glass Industry Leaders, vol. 38, Issue 10, 4 pgs. (Oct. 2003).

Taffera, T., "Fear Factor" DWM, Door & Window Maker Magazine, 9 pgs. (Apr.-May-Jun. 2002).

Ernst, R., "Sparklike's GasGlass is Put to the Test," US Glass, The Magazine of Influence for Glass Industry Leaders, vol. 36, Issue 9, 6 pgs. (Sep. 2001).

Ernst, R., "GasGlass - Sparklike" FDR Design Inc., Trip Report, 7 pgs. (Jul. 18, 2001).

Ernst., R., "First on the Scene—Putting Sparklike's Revolutionary Gas-Fill Detection Device to the Test," Door & Window Maker Magazine, 3 pgs. (Fall 2001).

Glass Build America, The Glass, Window & Door Expo, "Chart Your Course," 1 pg. (Mar. 10-12, 2004).

Freedman, A., et al., Aerodyne Research, Inc., Report, "Non-Intrusive Sensor for Gas Fill Verification of Insulated Glass Windows," 54 pgs. (Oct. 2003).

Sparklike, Ltd., "GassGlass-1001," Leaflet, 2 pgs. (2001-2002).

Sparklike, Ltd., "GasGlass—The New Way to Measure Your IG," Poster, 1 pg. (2000-2001).

Sparklike, Ltd., "GasGlass—The New Way of Measuring Your IG," Poster, 2 pgs. (Early 2000).

Sparklike, Ltd., "GasGlass Online," Poster, 1 pg. Birmingham Trade Show (2002).

Latta Dr., B., "Nonintrusive Test for Window Gas-Fill Level: Feasibility Study," Efficiency and Alternative Energy Technology Branch of Energy, Mines and Resources Canada, 45 pgs. (Feb. 1990).

IGMA Technical Services Committee Meeting, Agenda and Meeting Materials, 44 pgs. (Aug. 2001).

Reilly, S. Enermodal Engineering, Inc., "A Portable Device for Field Measurement of the Thermal Performance of Glazing Systems," 23 pgs. (Mar. 1993).

Glasstech 00, Show Poster, 1 page (2000).

Ernst, R., Answers from Sparklike LTD, 4 pgs. (Jul. 22, 2001).

* cited by examiner

METHODS AND APPARATUS FOR EVALUATING INSULATING GLASS UNITS

RELATED APPLICATIONS

This application is related to and claims priority to U.S. Provisional Application Ser. No. 60/482,127 by Trpkovski filed Jun. 24, 2003.

The entire disclosure of the above mentioned application is hereby incorporated by reference.

FIELD OF THE INVENTION

The present disclosure relates generally to methods and devices for evaluating insulating glass units in a production environment and in situ. More particularly, the present disclosure relates to methods and devices for evaluating the optical properties of insulating glass units.

BACKGROUND OF THE INVENTION

Insulating glass units (IGUs) are typically composed of two parallel glass panes spaced apart by a peripheral spacer. Spacers are typically made of metal, usually of tubular configuration, and are formed so as to have two flat sides that face the confronting surfaces of the glass panes. The spacers are bent so as to conform to the periphery of the glass panes. Typically, the spacers are adhered to the glass panes with a sealant that is gas-impermeable, such polyisobuytlene. An additional sealant, with strong adhesion force, such as silicone, is commonly applied around the outside edges of the IGU. For aesthetic purposes, muntins may be sandwiched between the panes to give the unit a divided light appearance. To improve thermal resistance across the glass assemblies, the space between the panes of glass, or interpane space, may be filled with an insulating gas such as argon. To perform adequately, the IGU must be filled with a proper amount of gas. Typically, the amount of gas flowed into the interpane space is gauged by flowing gas at a known rate for a specified period of time into the IGU.

Often, at least one pane surface of an insulating glass unit is coated with a low energy coating to prevent conduction of heat through the glass. These coatings can result in the reflectance of color from the glass surface. Typically, color reflectance is undesirable. Therefore, for aesthetic purposes, it is desirable to manufacture glass and IGUs that reflect at wavelengths in the blue or blue/green range.

In the manufacture of insulating glass units, uniform production lines are often used to produce large quantities of glass assemblies. In a typical production line, glass panes are transported to a conveyor with rollers on a vertical platen that transports the panes to a number of stations where various steps of the assembly process are performed.

In terms of quality assuring the reflected color of a IGU, for example, the methods have generally involved measuring the transmitted color of a coated glass pane before it is assembled into an IGU. Similarly, the gas fill concentration is typically quality controlled by procedures involving methods that destroy the IGU after the IGU has been fully assembled and removed from the production line. Therefore, materials are wasted and each unit cannot be quality assured.

It would be desirable therefore, to provide a quality control method that is capable of quality assuring each IGU produced in a non-destructive manner. Furthermore, to reduce costs, it would be desirable to provide an automated or semi-automated system on a production line that can quickly and accurately quality assure IGUs as they are manufactured without sacrificing materials, time, and labor expenses.

DETAILED DESCRIPTION

Figure 1:
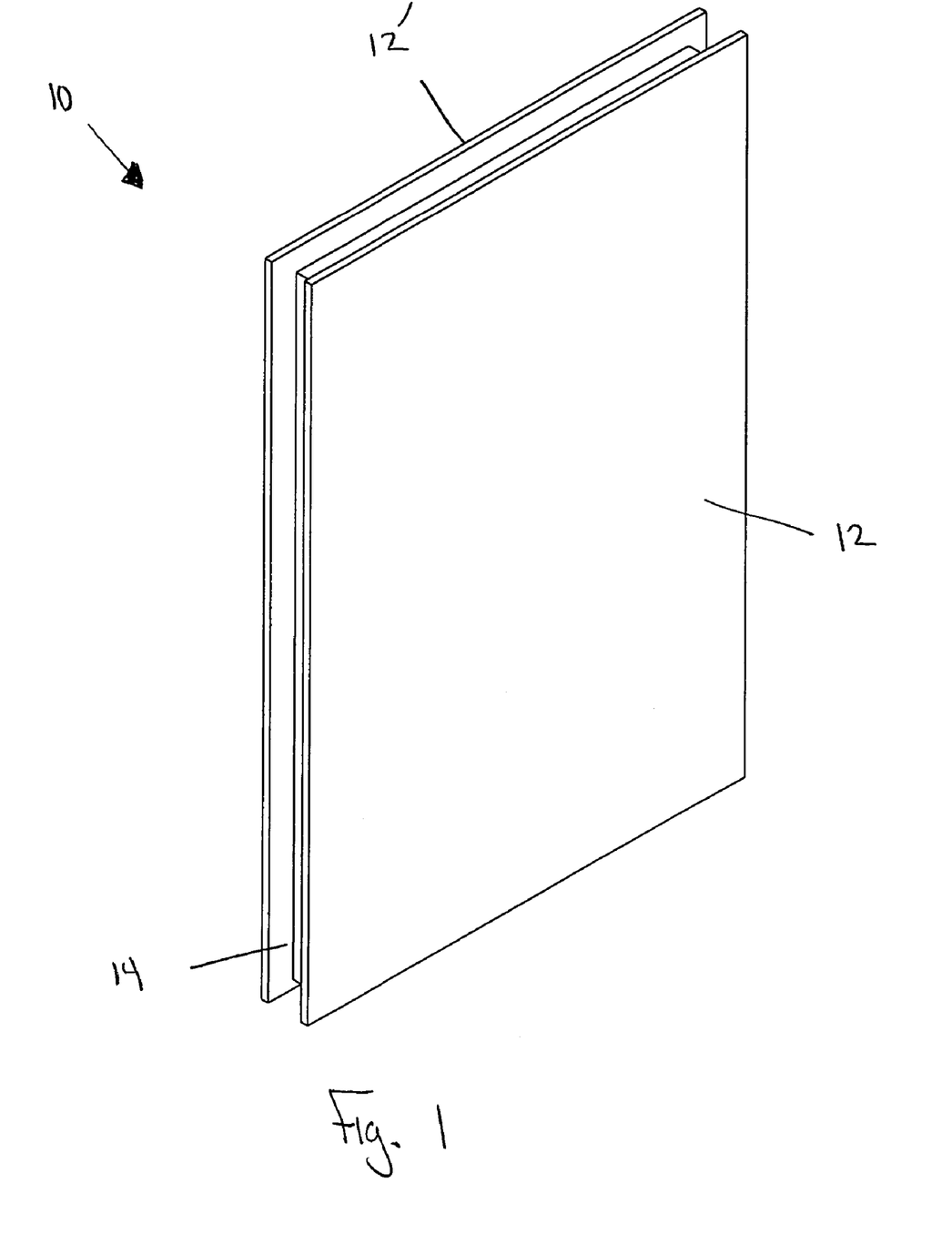
FIG. 1 depicts an insulating glass unit.

FIG. 1 illustrates one example of an insulating glass unit (IGU) 10, that can be provided according with the present invention. It is to be understood that the invention is not limited to practice with any particular type of IGU. To the contrary, all aspects of the present invention can be practiced in connection with insulating glass units of all types. Thus, the details of the illustrated IGUs should not be construed as limiting the scope of the present invention. Moreover, it is to be understood that, while the term insulating "glass" unit is used throughout the present disclosure, the panes 12 and 12' may be formed of materials other than glass for some applications.

The IGU 10 illustrated in FIG. 1 includes a first pane 12 and a second pane 12' together forming a pair of panes. The panes bound a between-pane space (i.e., an "interpane space" or "gas space") 14 therebetween and an exterior space thereabout. The panes are preferably spaced apart in a substantially parallel relationship by a spacer 18 (illustrated in FIG. 2). In more detail, the peripheral inner surfaces of the panes are joined by the spacer 18. Thus, the spacer 18 and the confronting inner surfaces of the panes 12, 12' together define the interpane space 14.

Figure 2:
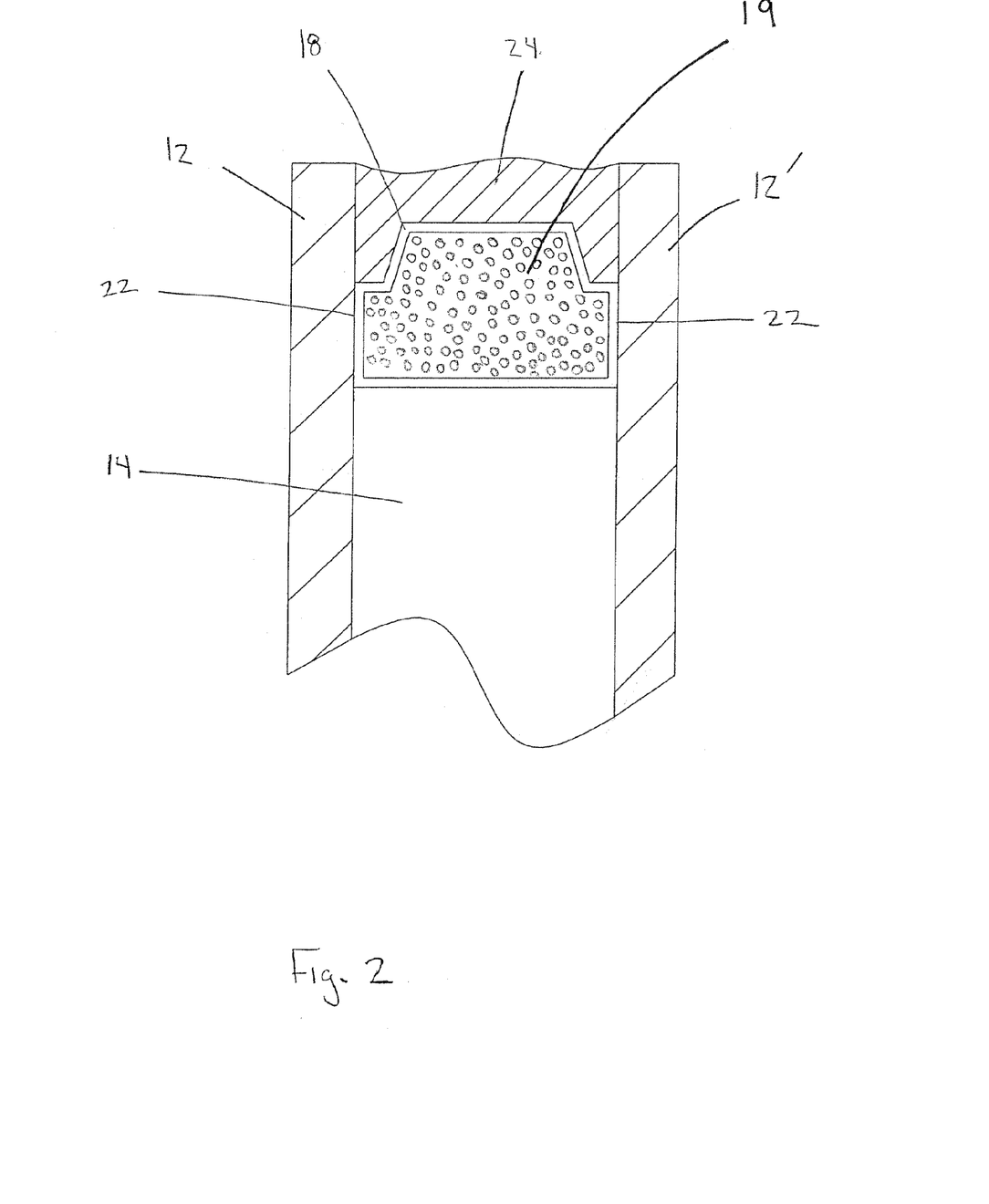
FIG. 2 is a cross-sectional illustration of the insulating glass unit shown in FIG. 1.

Typically, the spacer 18 is formed of a metallic tubing (e.g., aluminum, stainless steel and others). This tubing can be provided in a variety of cross-sectional configurations. Examples of spacers that may be suitable in some applications are disclosed in U.S. Pat. Nos. 5,377,473; 5,439,716; 5,679,419; 5,705,010, and 5,714,214, the entire teachings of each of which are incorporated herein by reference. It is also noted that a variety of conventional spacer designs are commercially available from Alumet Manufacturing, Inc., which is located in Marysville, Wash., U.S.A.

Regardless of the particular spacer configuration, the spacer characteristically includes two generally opposed lateral surfaces that are adapted to be bonded respectively to the peripheral inner surfaces of the panes. Bonding the spacer to both panes desirably forms a gas-tight seal that prevents air and other gases from entering and/or escaping the interpane space. The interior of the spacer desirably carries a deposit of desiccant 19 (best shown in FIG. 2). The desiccant 19 is preferably provided in a flowable form (e.g., in a granular or powdered form), to facilitate flowing desiccant into the interior of the spacer. Desiccants of this nature are conventional in the present art and are available through a number of commercial suppliers.

The sealing system of an IGU 10 desirably minimizes gas flow between the gas space inside the unit and the ambient environment outside the unit. While some IG units have only a single seal, other IG units typically include two seals: a primary or "first" seal 22 and a secondary or "second" seal 24, better illustrated in the cross section of FIG. 2. The first seal 22 is preferably formed of material that is resistant to permeation of air, moisture, and any insulative gas fill. For example, this seal can be advantageously formed of a butyl sealant (e.g., polyisobutylene). The second seal 24 is preferably formed of material that has good adhesive properties. For example, this seal 24 can be formed of silicone, polysulfide, polyurethane, or any other material that bonds adhesively with the spacer and panes. Thus, the spacer 18, together with the first 22 and second 24 seals, isolates the gaseous atmosphere within the interpane space 14 from the ambient atmosphere of the exterior space.

The interpane space 14 of an IGU 10 can be advantageously filled with an insulative gas. It is to be understood that the term insulative gas is used herein to refer to any gas that is a better thermal insulator than air. For example, a gas is to be considered insulative if it has a lower thermal conductivity than air, and hence reduces (relative to an IGU containing air) heat transfer by conduction. A gas is also to be considered insulative if it is heavier than air, and hence reduces (relative to an IGU containing air) heat transfer by convection. For example, argon is a preferred insulative gas since it is both less thermally conductive and heavier than air. Other inert gas fills can be used as well. Argon, krypton, and other inert gases are commercially available from a number of suppliers, including BOC Gases (Murray Hill, N.J., U.S.A.), Air Products and Chemicals, Inc. (Allentown, Pa., U.S.A.), and Air Liquide America Corporation (Cambridge, Md., U.S.A.).

Figure 3:
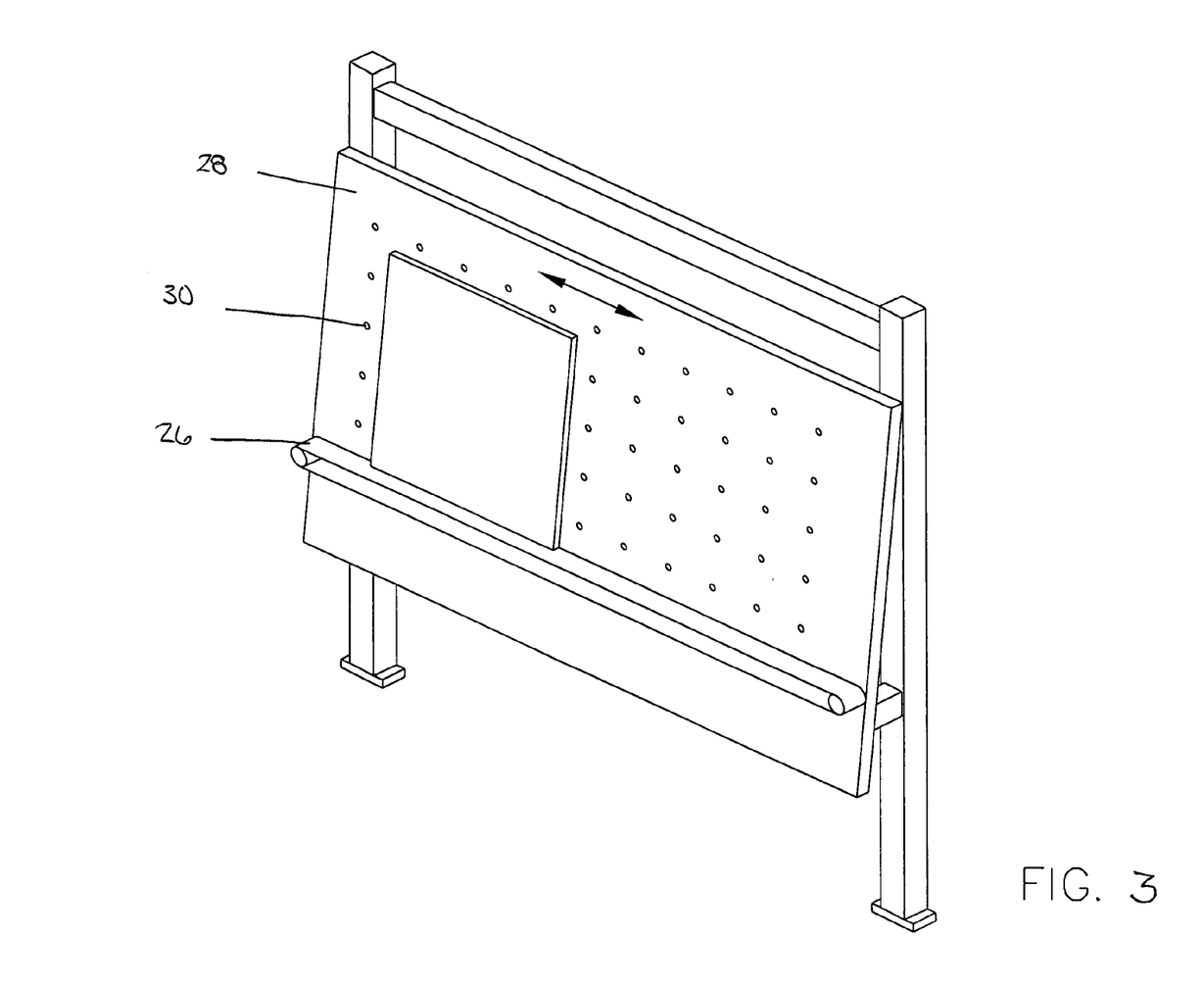
FIG. 3 depicts a conveyer for use on an insulating glass unit production line.

IGUs of standard size can be assembled on IGU production or assembly lines. FIG. 3 illustrates generally a production line for manufacturing IGUs. Typically, if the IGU 10 is to comprise glass panes with a coating, the coating is applied to the panes prior to assembly of the IGU.

It is to be understood that the following description of an IGU production is illustrative only and the invention is not limited to use on a production line generally or to use on any particular production line. The assembly line and assembly stations described herein may be varied with the addition or deletion of various stations.

The glass panes are typically manually loaded onto a conveyor 26 that transports the panes and partially assembled units to various stations for processing. The conveyor 26 may be comprised of a generally horizontal belt or other suitable solid surface to support the bottom surface of the glass panes or partially assembled units. A generally vertical platen 28 with a plurality of rollers 30 for vertical support and propulsion of the panes or partially formed propels the glass panes or partially formed IGUs through the production line.

In an illustrative production line, for example, the glass panes may be conveyed to a variety of stations including, for example, an edge deletion station where, if present, the coating on the glass is removed from the perimeter of the pane. The edge deleted glass pane may then be conveyed to a washing station to remove any debris or unwanted material from the surface of the pane. A gas-impermeable sealant is applied to the edges of a spacer dimensioned to the particular configuration of the IGU are adhered to the periphery of the one pane of a pair of panes.

Pairs of panes, one pane with a spacer adhered and a bare pane may be next conveyed to an assembly station (not shown) where the pairs are mated and joined together through the exposed primary sealant on the edge of the spacer opposing the edge adhered to the glass pane.

The partially assembled IGUs are then conveyed to a gas-fill station where typically, an insulating gas is inserted into the interpane space and the unit is sealed. One exemplary mechanism for filling IGUs is disclosed in U.S. Pat. No. 5,957,169, the entire disclosure of which is hereby incorporated by reference.

Figure 4:
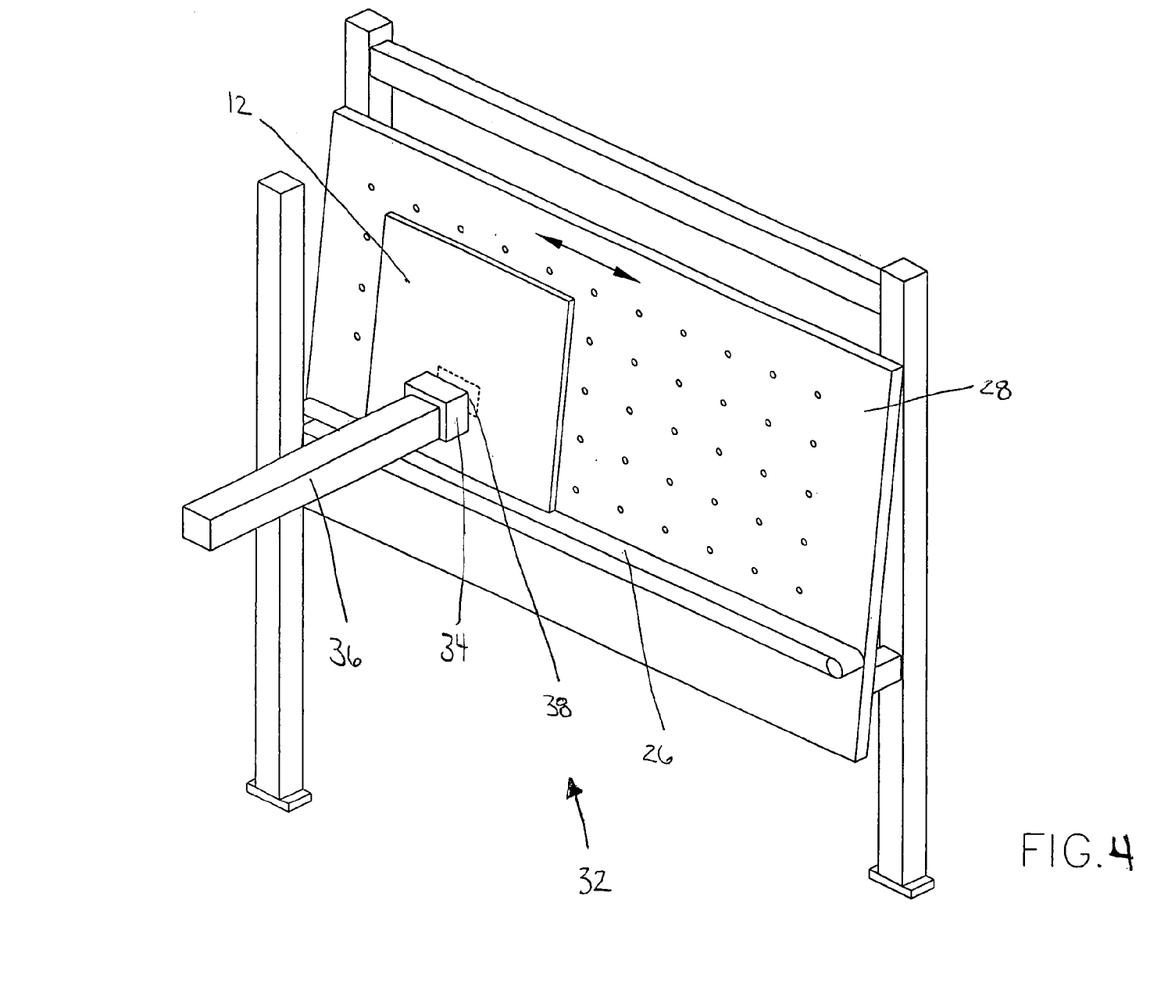
FIG. 4 is a schematic of a color measuring station on an insulating glass unit production line according to an embodiment of the present invention.

FIG. 4 illustrates a color measuring station 32 positioned downstream from a gas fill station. After an IGU 10 is filled with gas and sealed, it is conveyed to the color measuring station 32 where the color of a reflected light emission that has been transmitted through the glass panes is measured. Alternatively, the IGUs may be manually transported by personnel to the station 32.

A color change produced by the coated substrates of the IGU may be measured by using devices that transmit light that has a known wavelength distribution over the visible spectrum. The light from the source may strike the coated substrate at an angle that is generally perpendicular to the surface of the substrate. A light detector may measure the light intensity at various wavelengths across the visible spectrum and compare these measurements to the known wavelength distribution of the source to determine one or more optical characteristics of a sample being evaluated Color measuring station 32 of figure for comprises a color measuring device 34. Color measuring device 34 may comprise various instruments without deviating from the spirit and scope of the present invention. Examples of instruments that may be suitable in some applications include calorimeters and spectrophotometers. For example, an apparatus in accordance with some embodiments of the present invention may comprise various commercially available spectrophotometers. One spectrophotometer that may be suitable for some applications is commercially available from Minolta Camera company of Osaka, Japan which identifies it with the model number CM-2500D. Color measuring instruments are described in a number of U.S. Patents, including: U.S. Pat. Nos. 4,397,533; 4,402,611; 4,917,495; 4,995,727; 5,168,155; 5,214,494; 5,432,609; 5,570,192; 5,592,294; 5,831,740; 5,859,709; 5,963,334; 5,978,606; 6,020,959; 6,088,117; 6,462,819; 6,614,518; and 6,707,553. The entire disclosure of each U.S. Patent listed above is hereby incorporated by reference.

Color measuring device 34 can be coupled to the production line by any suitable means. For example, as shown in FIG. 4, the color measuring device 34 may be attached to a manually or automated extendable arm 36 provided adjacent to the conveyer 26. The extendable arm 36 may be movable perpendicularly with respect to the surface of the IGU so that the color measuring device 34 moves towards the surface of a glass pane 12 as the IGU enters the station 32 to facilitate the measurement. The extendable arm 36 includes an engagement surface (not shown) for engaging and securing the IGU 10 during measurement. The engaging surface should contact the glass surface and apply a pressure that is suitable for securing the unit without damaging the unit. A force of about 10 psi may serve both requirements in some applications. To further protect the IGU, the engaging surface may be covered with a soft material, for example, felt, so that it does not damage the glass surface.

In some embodiments of the present invention, a reflecting surface may be provided on a surface opposing the detector. For example, a reflecting tile 38 may be provided on the vertical platen 28 in alignment with the detector of the color measuring device 34.

Figure 5:
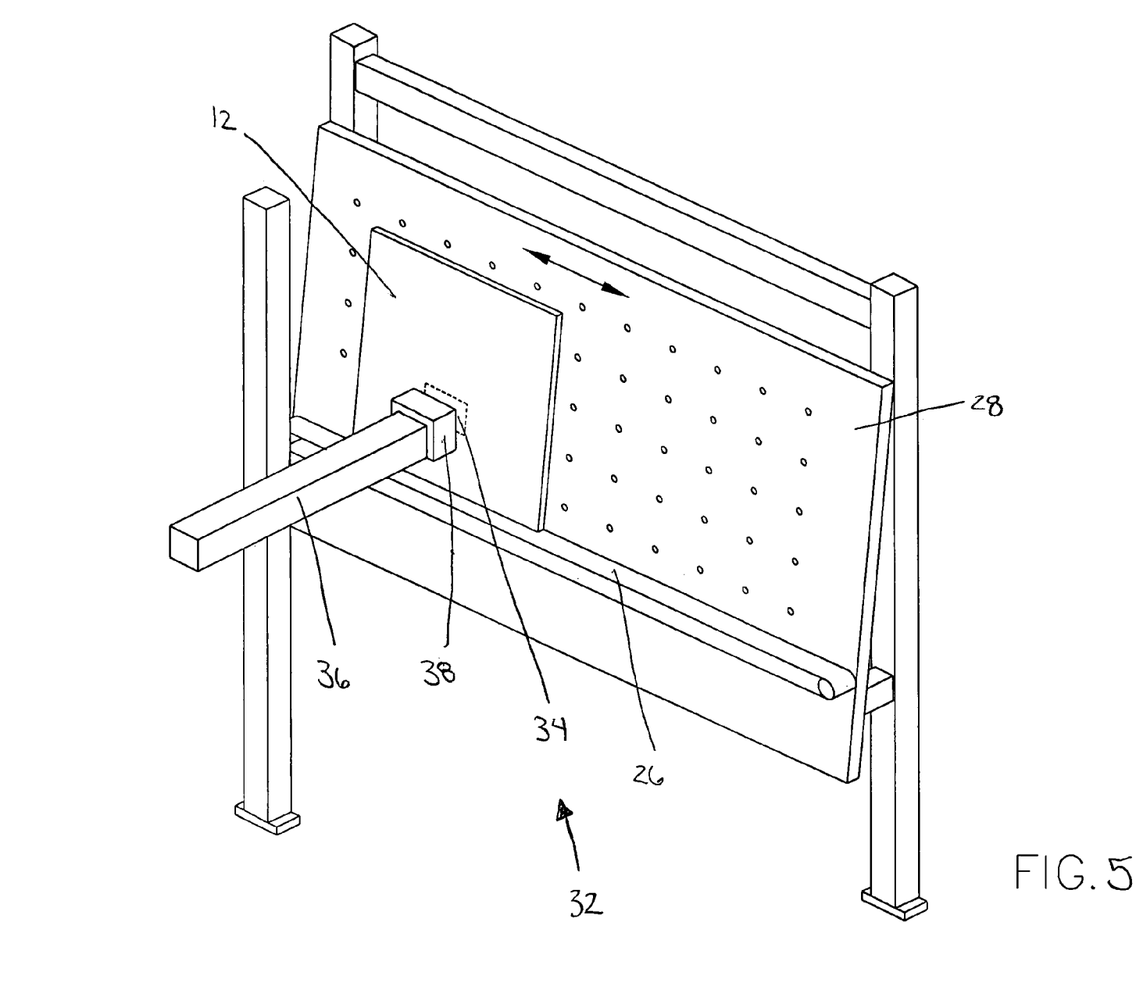
FIG. 5 is an alternative embodiment of the color measuring station shown in FIG. 4.

FIG. 5 illustrates an alternative embodiment wherein the color measuring device 34 is attached to the vertical platen 28 and the reflecting tile 38 is provided on the opposing side of the IGU 10, for example, by attachment to an extendable arm 36 or other structure.

Coatings are typically applied to the #2 surface of panes, which is the interior surface of the pane of glass facing the exterior of the building. The coating often results in the reflectance of color to the eye of an observer. Such coloration can be problematic and detract from the architectural beauty of a building. Generally, it is desirable to provide IGUs that are aesthetically pleasing to people observing the exterior of the building into which the IGU is incorporated. Therefore, advantageously, in practicing the invention, according to any embodiment, the glass sheets may be loaded onto the production line so when the IGU 10 reaches the color measuring station 32, the IGU 10 is positioned so that the device for measuring color 34 detects the transmitted color from the #2 surface through the #1 surface. In this configuration, the color visible from the exterior of the building will be monitored.

In operation, as an IGU 10 enters the station 32 it is positioned so that a portion of the glass surface 12 is aligned with the color measuring device. The extendable member 36 moves towards the IGU 10 and contacts the glass pane 12 closest to it with the soft surface (not shown). The extendable member 36 stabilizes the IGU 10 against the vertical platen 28 while the reading is made. The color measuring device 34 emits radiation towards the IGU. This radiation travels through the panes 12 and 12' and space 14 until it reaches the tile 38. The radiation striking the tile 38 is reflected back to a detector on the color measuring device 34 and the appropriate correlations are made.

Figure 6:
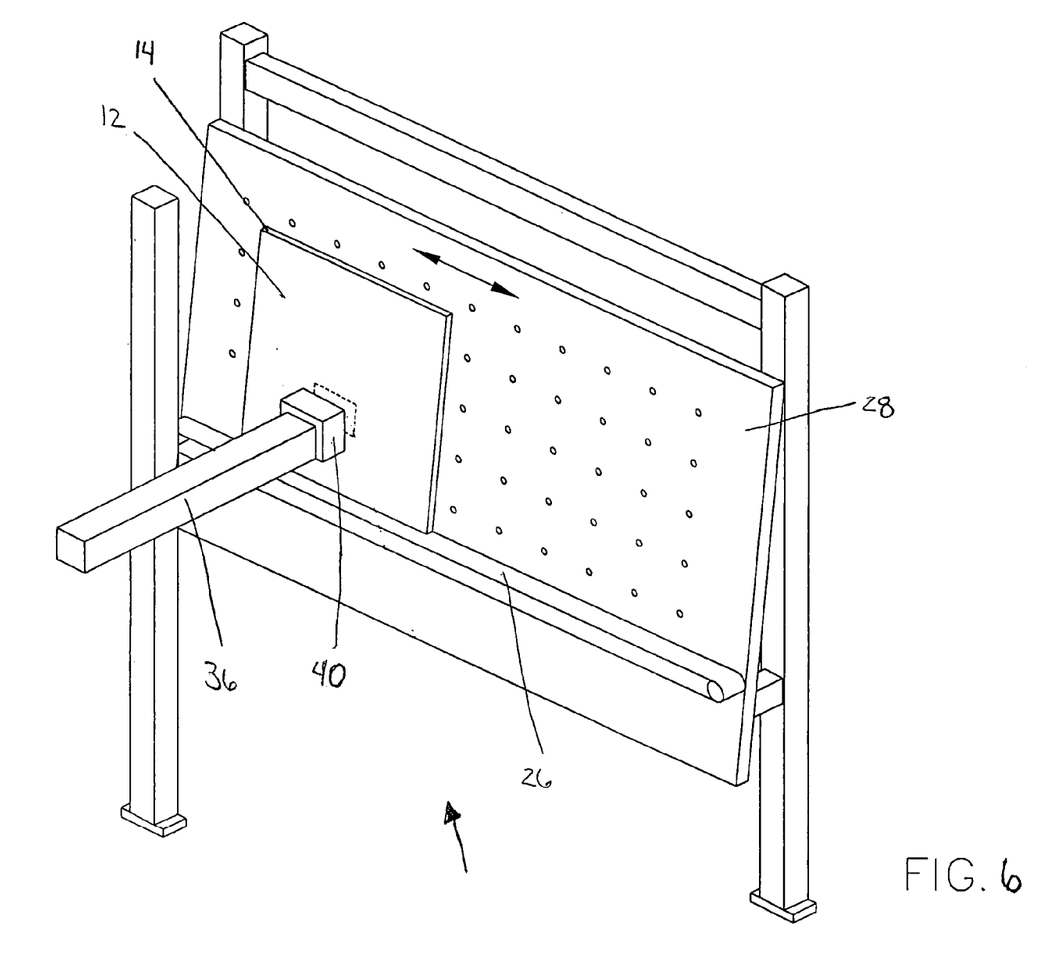
FIG. 6 is a schematic of a gas fill concentration measuring station on an insulating glass unit production line according to an embodiment of the present invention.

FIG. 6 illustrates an alternative embodiment where a gas fill concentration measuring device 40 is provided at a station 42 positioned downstream from a gas fill station (not shown). The gas fill concentration measuring device 40 measures the concentration of the gas in the interpane space in a fashion that does not compromise the integrity of the assembled IGU. Use of a non-destructive method allows for each unit to be quality assured before it reaches the customer. An example of such a gas fill concentration device is the GasGlass-1001 commercially available from Sparklike, Ltd., of Helsinki, Finland.

The gas fill concentration measuring device 40 may be secured to the production line in any matter suitable to bring it into proximity to the IGU 10 to be measured. For example, the device 40 may be attached to an extendable arm 36, similar to the color measurement device, provided adjacent to the production line. The extendable arm 36 may be movable perpendicularly with respect to the surface of a glass pane 12 of the IGU 10 so that it may move into proper position to take the reading.

When an IGU reaches the station, the extendable member 36 is activated and moves toward the IGU 10 bringing the gas fill concentration measuring device 40 into contact with the surface of the glass pane 12 of the IGU 10. The gas fill concentration measuring device 40 may include a means for engaging the glass surface, for example a suction cup, so that a measurement may be initiated. After the measurement is made, the IGU 10 is conveyed out the station 42 or alternatively, is manually removed.

Figure 7:
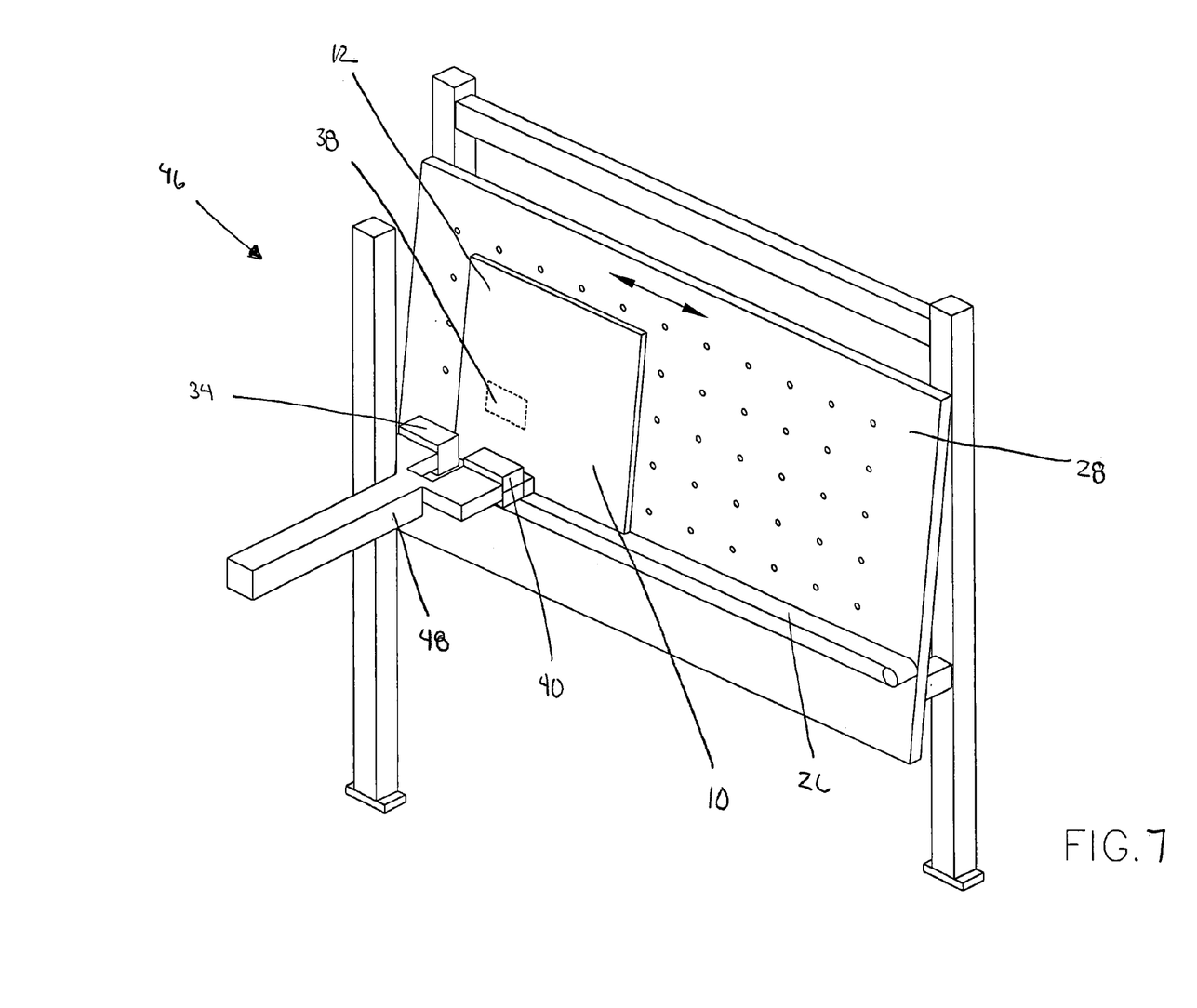
FIG. 7 is a schematic of a dual color and gas fill measuring station provided on an insulating glass unit production line according to an embodiment of the present invention.

FIG. 7 illustrates an alternative embodiment where the station 46 includes both a color measuring device 34 and a gas fill concentration measuring device 40. The dual measuring station 46 is positioned downstream from a gas fill station so that the IGUs are least partially assembled and filled with gas as they move through the production line.

The color measuring device 34 and gas fill concentration sensor 40 may be mounted to an extendable arm 48 coupled to the conveyor 26 adjacent to the IGU 10. A reflecting tile 38 may be provided on the vertical platen 28 in alignment with the color measuring device to facilitate the measurement as previously described. The extendable arm 48 may include an engaging surface for contacting and stabilizing the IGU while the measurements are taken.

In an alternative embodiment, the color measuring device is mounted to the vertical platen 28 and a color reflecting tile 38 is mounted on the extendable member 48 in alignment with the color measuring device 34 and the gas fill concentration sensor 40 is mounted on the extendable member 48 (as described above).

Figure 8:
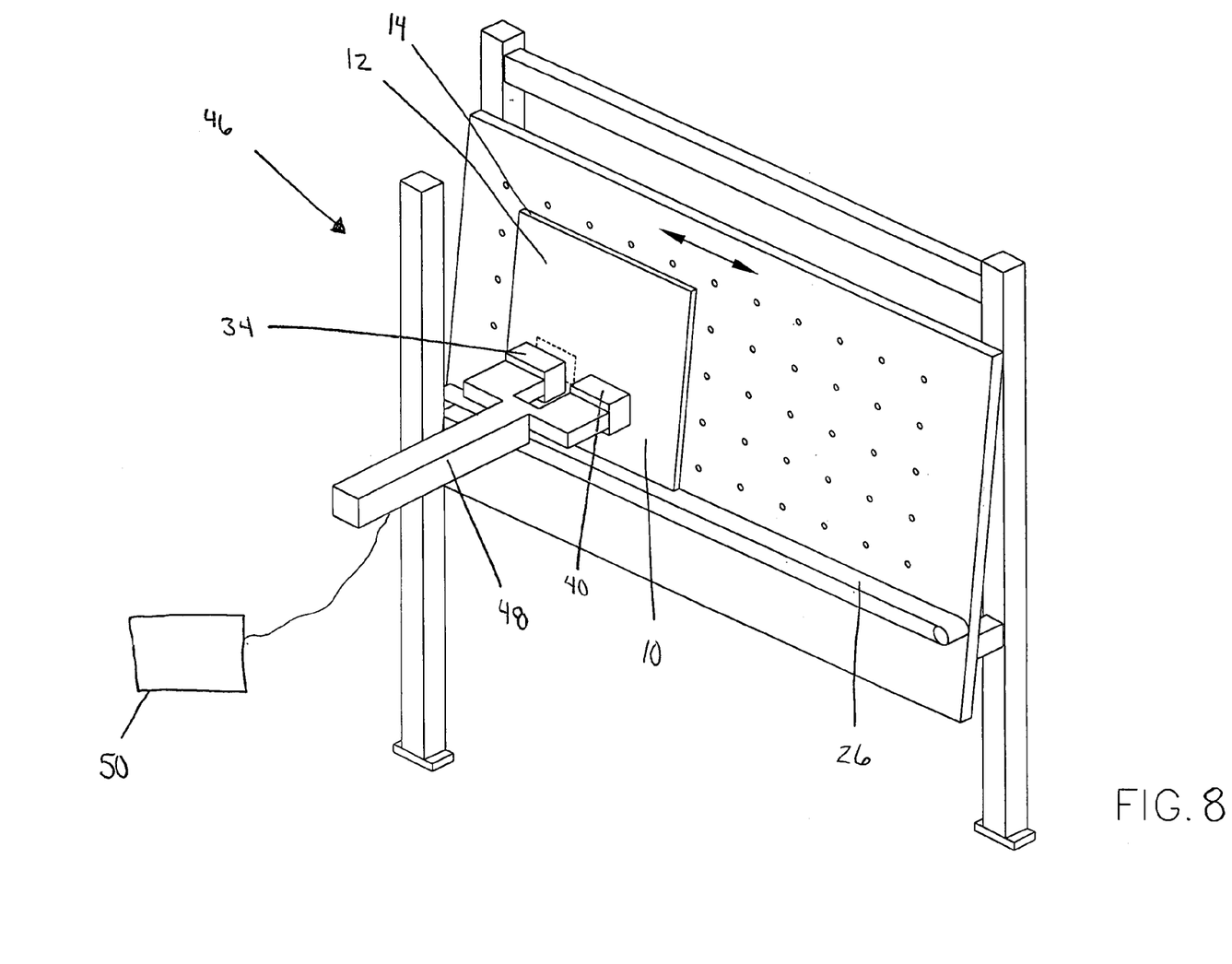
FIG. 8 illustrates the embodiment of FIG. 7 in operation.

FIG. 8 illustrates the embodiment of FIG. 7 in operation. When an IGU 10 present on the conveyer 26 reaches the station 46, the conveyer 26 is stopped so that the measurements may be taken. The extendable arm 48 carrying the color measuring device 34 and gas fill concentration measuring device 40 is activated and moved toward the glass surface 12 so that the engagement surface (not shown) contacts the glass surface. The extendable arm 48 may be moved in either the X or Y axis (of the glass pane surface) to avoid any obstructions, such as muntin bars. Once the positioning is satisfactory, the color measuring device 34 is activated and the color reading taken. Next, the gas fill concentration measuring device 40 is moved towards the glass pane surface 12 where the suction cup or other suitable gripping means engages the glass surface 12. The gas fill concentration measurement device is activated to take a measurement. The measurements may be taken in various sequences. For example, the gas fill concentration may be measured first, or alternatively, both measurements may be taken simultaneously.

Positioning the station at a location downstream from the gas fill station provides the advantage of measuring the gas fill concentration and color of IGUs after complete assembly but before any masking material, which may interfere with measurements, is applied to the IGU.

Reductions in manual labor and time required necessary to produce IGUs is desirable as cost reducing measures. Providing a dual color and gas fill measuring station on the IGU production line allows for efficient, time effective manufacture and quality assurance. Both the reflected color and gas fill can be evaluated at a single stop, reducing production costs by automating quality assurance procedures and reducing the time required to carry out the procedure. The stop period, that is, the time an IGU will spend at the color and gas fill concentration center, is preferably less than 30 seconds and more preferably is in the range of 10–20 seconds.

The data obtained from the measuring devices according to any embodiment described herein, can be captured and transmitted to a database 50. The measuring devices 34 and 40 may be coupled to the data base 50, for example, a personal computer or alternatively the data may be transmitted telemetrically. The stored data can be used for a variety of purposes. For example, stored data can be used for quality control to monitor the retention of gas within the IGU. The gas concentration of an IGU can be measured at any time subsequent to manufacture and compared against the concentration at the time of manufacture to determine whether the IGUs are properly retaining the gas. The stored data may be used for a variety of other purposes as is appreciated by the skilled artisan.

Figure 9:
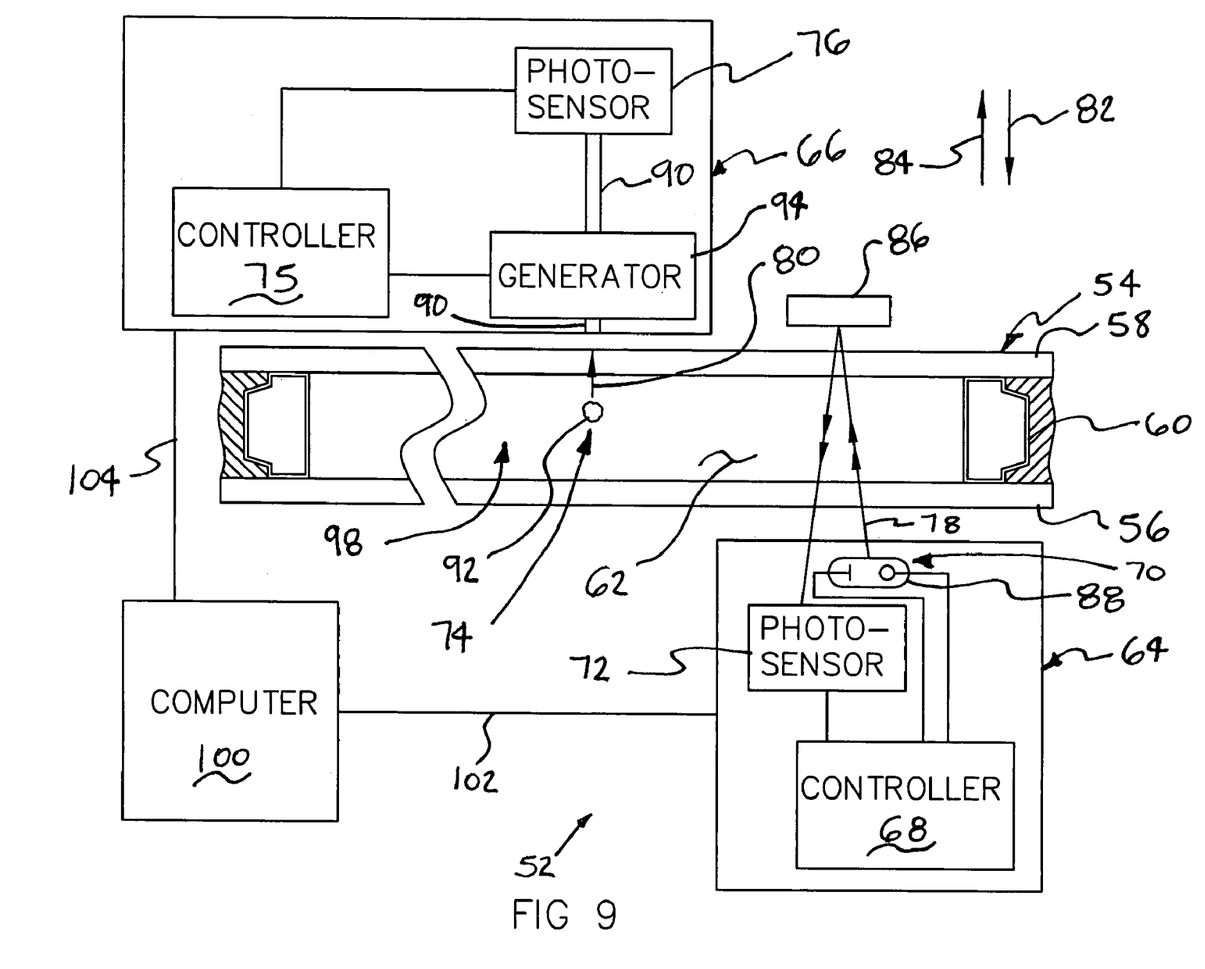
FIG. 9 is a schematic diagram of an apparatus in accordance with an additional exemplary embodiment of the present invention.

FIG. 9 is a schematic diagram of an apparatus 52 for evaluating an insulating glass unit 54. Insulating glass unit 54 comprises a first pane 56, a second pane 58 and a spacer 60 interposed between first pane 56 and second pane 58. First pane 56, second pane 58, and spacer 60 define an interpane space 62. Apparatus 52 comprises a color measuring device 64 and a gas fill concentration measuring device 66. Color measuring device 64 comprises a first controller 68, a first light source 70 and a first photosensor 72.

As shown in FIG. 9, first light source 70 of color measuring device 64 is disposed outside of interpane space 62 of insulating glass unit 54. A first light emission 78 produced by first light source 70 is illustrated using arrows in FIG. 9. In FIG. 9, light from first light emission 78 is shown traveling in a first direction 84 as it passes through first pane 56 and second pane 58 before striking a reflective tile 86. Also in FIG. 9, light from first light emission 78 is shown traveling in a second direction 82 as it passes through second pane 58 (a second time) and first pane 56 (a second time) before striking first photosensor 72.

First light source 70 may comprise various light sources without deviating from the spirit and scope of the present invention. In the embodiment of FIG. 9, first light source 70 comprises a xenon flash lamp 88. It is also important to note that reflective tile 86 may comprise various reflective surfaces without deviating from the spirit and scope of the present invention. In some implementations, for example, reflective tile 86 may comprise a white surface.

In the embodiment of FIG. 9, gas fill concentration measuring device 66 comprises a second controller 75 and a second photosensor 76 that is capable of sensing light from a second light emission 80. In the embodiment of FIG. 9, light from a second light emission 80 is carried to second photosensor 76 by a fiberoptic cable 90. It is important to note that various embodiments of first photosensor 72 and second photosensor 76 are possible without deviating from the spirit and scope of the present invention. In some embodiments, for example, these photosensors may comprise a plurality of filters having different spectral transmittances and a plurality of photodiodes that are arranged to be illuminated by light that has passed through selected filters.

In FIG. 9, second light emission 80 is produced by a plasma 92 that is disposed within interpane space 62 of insulating glass unit 54. Plasma 92 may be identified as a second light source 74. In the embodiment of FIG. 9, gas fill concentration measuring device 66 comprises a field generator 94 that is capable of exciting a gas 98 disposed in interpane space 62 to form plasma 92. Also in the embodiment of FIG. 9, generator 94 is capable of generating an oscillating magnetic and/or electromagnetic field proximate an outer surface 96 of insulating glass unit 54.

Generators are described in a number of U.S. Patents, including: U.S. Pat. Nos. 5,303,139; 6,538,388; 6,567,278; 6,586,887; 6,727,654; 5,712,592; and 6,750,614. The entire disclosure of each U.S. Patent listed above is hereby incorporated by reference.

In the embodiment of FIG. 9, both color measuring device 64 and gas fill concentration measuring device 66 are connected to a computer 100. Computer 100 may comprise various elements without deviating from the spirit and scope of the present invention. Examples of elements that may be suitable in some applications include a personal computer, a microprocessor, and a microcontroller.

In the embodiment of FIG. 9, color measuring device 64 is shown providing a first signal 102 to computer 100 and gas fill concentration measuring device 66 is shown providing a second signal 104 to computer 100. First signal 102 may be, for example, representative of light sensed by first photosensor 72 from first light emission 78. Second signal 104 may be, for example, representative of light sensed by second photosensor 76 from second light emission 80.

In some embodiments of the present invention, computer 100 may decide to accept or reject insulating glass unit 54 based upon both first signal 102 and second signal 104. For example, computer 100 may be capable of comparing first signal 102 with a first acceptable range and comparing second signal 104 with a second acceptable range. Computer 100 may then generate a reject signal if first signal 102 is outside the first acceptable range or if second signal 104 is outside the second acceptable range.

In some embodiments of the present invention, computer 100 may be capable of correcting second signal 104 to compensate for a color change that occurs in second light emission 80 as it passes through a single pane of insulating glass unit 54. For example, computer 100 may use a color change that occurs in light from first light emission 78 as it passes through first pane 56 and second pane 58 a first time and a second time. The color change may be calculated by comparing a known color of light emitted by first light source 70 to the color of light received by first photosensor 72. This comparison may include adding and/or subtracting color components. The color of light received by second photosensor 76 may be determined from second signal 104. One quarter of the color change may be subtracted from and/or added to the color of light received by second photosensor 76 to correct for a color change that occurs in second light emission 80 as it passes through a single pane of insulating glass unit 54.

While a preferred embodiment of the invention has been disclosed, it should be understood that various changes, adaptations, and modifications may be made therein without departing from the spirit of the invention and the scope of the appended claims.

What is claimed is:

1. A system for producing insulating glass units in a production line environment, the system comprising:
   a conveyer for transporting components that form the insulating glass units as well as the insulating glass units themselves to stations located along the production line; and
   a spectrophotometer located at a station of the production line wherein the spectrophotometer measures a color characteristic of a reflected light emission of an insulating glass unit delivered to that station.

2. The system of claim 1, further comprising an extendable member located at the station with the spectrophotometer, wherein the extendable member contacts and secures the insulating glass unit that arrives at the station when the spectrophotometer measures the color characteristic of the insulating glass unit.

3. The system of claim 2, wherein the spectrophotometer is coupled to the extendable member.

4. The system of claim 3, wherein the extendable member is moveable in at least the X or Y axis relative to the insulating glass unit.

5. The system of claim 1, further comprising means for storing a result of a measurement taken by the spectrophotometer.

6. The system of claim 1, further comprising a reflecting tile for reflecting light transmitted through the insulating glass unit to a light detector of the spectrophotometer.

7. A system for measuring gas fill concentration and color of insulating glass units during manufacture thereof in a production line environment, the system comprising:
   a conveyer for transporting components that form the insulating glass units as well as the insulating glass units themselves to stations located along the production line; and
   a spectrophotometer and a gas fill concentration sensor both located at a station of the production line wherein the spectrophotometer measures a color of a reflected light emission of an insulating glass unit and the gas fill concentration sensor measures the gas fill concentration of the insulating glass unit.

8. The system of claim 7, wherein the spectrophotometer and gas fill concentration sensor operate during a single stop period.

9. The system of claim 8, wherein the stop period is in the range of 10–20 seconds.

10. The system of claim 7, further comprising an extendable member located at the station with the spectrophotometer and the gas fill concentration sensor wherein the extendable member contacts and secures the insulating glass unit while color and gas fill concentration of the insulating glass unit are measured.

11. The system of claim 10, wherein the extendable member further includes the gas fill concentration sensor and spectrophotometer coupled thereto.

12. The system of claim 11, wherein the extendable member is moveable in at least the X or Y axis relative to the surface of the insulating glass unit.

13. A method for measuring gas fill concentration and color of insulating glass units during manufacture thereof, the method comprising the steps of:
   conveying the gas-filled insulating glass unit to a color and gas fill concentration measuring station to obtain a color measurement and a gas fill measurement;
   measuring the color and gas fill concentration of the insulating glass unit at the color and gas fill concentration measuring station,
   determining whether the color and gas fill concentration measurements are within acceptable ranges; and
   accepting or rejecting the insulating glass unit.

14. The method of claim 13, further comprising the step of securely positioning the insulating glass unit at the color and gas fill concentration measuring station prior to measuring the color and gas fill concentration.

15. The method of claim 13, wherein the step of measuring the color comprises measuring the color from a #2 surface of the insulating glass unit.

16. The method of claim 13, further comprising the step of transmitting color and gas fill concentration data to a database for storage.

17. A method for manufacturing insulating glass units, the method comprising:
   coupling two panes of glass together to create an interpane space therebetween;
   filling the interpane space with insulating gas to produce a partially formed insulating glass unit;
   measuring a color characteristic and gas fill concentration of the partially formed insulating glass unit at a single station on a production line,
   determining whether the color characteristic and gas fill concentration are within acceptable ranges;
   accepting or rejecting the insulating glass unit.

18. The method of claim 17, further comprising transmitting color and gas fill concentration data to a data base for storage.

19. The method of claim 17, wherein the step of measuring the color characteristic comprises measuring the color from a #2 surface of the insulating glass unit.

20. A system for producing insulating glass units in a production line environment, the system comprising:
   a spectrophotometer positioned at a station of the production line, wherein an insulating glass unit is conveyed to the spectrophotometer station, the spectrophotometer being configured to measure a color of the insulating glass unit; and
   a gas fill concentration sensor positioned at the production line, wherein the insulating glass unit is conveyed to the gas fill concentration sensor station, the gas fill concentration sensor being configured to measure the gas fill concentration of the insulating glass unit.

21. The system of claim 20, further comprising an extendable member located proximate to the spectrophotometer and to the gas fill concentration sensor.

22. The system of claim 21, wherein the spectrophotometer and the gas fill concentration sensor are both coupled to the extendable member.

23. The system of claim 22, wherein the extendable member is movable in at least the X or Y axis relative to the insulating glass unit.

24. A method for evaluating an insulating glass unit comprising the steps of:
   emitting a first light emission from a first light source disposed outside of an interpane space of the insulating glass unit;
   sensing light from the first light emission that has passed through at least a portion of the insulating glass unit
   emitting a second light emission from a second light source disposed within an interpane space of the insulating glass unit;
   sensing light from the second light emission that has passed through at least a portion of the insulating glass unit;
   determining whether light sensed from the first light emission and light sensed from the second light emission are within acceptable ranges; and
   accepting or rejecting the insulating glass unit.

25. The method of claim 24, wherein a color of the first light emission is known and a color of the second light emission is unknown.

26. The method of claim 24, wherein the step of sensing light from the first light emission that has passed through at least a portion of the insulating glass unit comprises the step of sensing light from the first light emission that has passed through a first pane and a second pane of the insulating glass unit.

27. The method of claim 26, wherein the step of sensing light from the first light emission comprises the step of sensing light from the first light emission that has passed through the first pane and the second pane of the insulating glass a second time after being reflected by a reflective surface.

28. The method of claim 24, wherein the step of sensing light from the second light emission that has passed through at least a portion of the insulating glass unit comprises the step of sensing light from the second light emission that has passed through a single pane of the insulating glass unit.

29. The method of claim 24, wherein the first light source comprises a xenon flash lamp.

30. The method of claim 24, wherein the second light source comprises a plasma.

31. The method of claim 24, wherein the step of emitting a second light emission from the second light source comprises the step of exciting a gas disposed in the interpane space to form a plasma.

32. The method of claim 31, wherein the gas disposed in the interpane space comprises argon.

33. The method of claim 31, wherein the step of exciting the gas disposed in the interpane space comprises the step of generating an oscillating magnetic field proximate an outer surface of the insulating glass unit.

34. The method of claim 24, further including the step of providing a first signal to a computer, wherein the first signal is based on light sensed from the first light emission.

35. The method of claim 34, further including the step of providing a second signal to a computer, wherein the second signal is based on light sensed from the second light emission.

36. The method of claim 35, further including the step of rejecting or accepting the insulating glass unit based upon both the first signal and the second signal.

37. The method of claim 35, further including the step of deciding whether to accept the insulating glass unit based upon both the first signal and the second signal.

38. The method of claim 35, further including the steps of:
comparing the first signal with a first acceptable range;
comparing the second signal with a second acceptable range; and
generating a reject signal if the first signal is outside the first acceptable range or if the second signal is outside the second acceptable range.

39. The method of claim 35, further including the steps of:
comparing the first signal with a first acceptable range;
comparing the second signal with a second acceptable range; and
generating an accept signal if the first signal is within the first acceptable range and the second signal is within the second acceptable range.

40. The method of claim 35, further including the step of correcting the second signal to compensate for a color change occurring in light from the second light emission as the light passes through a single pane of the insulating glass unit.

41. The method of claim 40, wherein the step of correcting the second signal comprises the step of calculating a color change that occurs in light from the first light emission as it passes through at least a portion of the insulating glass unit.

42. The method of claim 41, wherein the step of calculating a color change that occurs in light from the first light emission comprises the step of comparing a known color of light emitted by the first light source with a color of light received by a first photosensor.

43. An apparatus for evaluating an insulating glass unit, comprising:
a first light source disposed outside of an interpane space of the insulating glass unit for emitting a first light emission;
a first photosensor for sensing light from the first light emission that has passed through at least a portion of the insulating glass unit;
a means for emitting a second light emission from within the interpane space of the insulating glass unit; and
a second photosensor for sensing light from the second light emission that has passed through at least a portion of the insulating glass unit.

44. The apparatus of claim 43, wherein a color of the first light emission is known and a color of the second light emission is unknown.

45. The apparatus of claim 43, wherein the first photosensor is positioned so as to sense light from the first light emission that has passed through a first pane and a second pane of the insulating glass unit.

46. The apparatus of claim 43, further comprising a reflective tile disposed proximate the insulating glass unit.

47. The apparatus of claim 46, wherein the reflective tile and the first photosensor are disposed on opposite sides the insulating glass unit relative with one another.

48. The apparatus of claim 46, wherein the reflective tile and the first photosensor are generally aligned with one another.

49. The apparatus of claim 46, wherein the reflective tile comprises a white surface.

50. The apparatus of claim 43, wherein the second photosensor is positioned so as to sense light from the second light emission that has passed through a single pane of the insulating glass unit.

51. The apparatus of claim 43, wherein the first light source comprises a xenon flash lamp.

52. The apparatus of claim 43, wherein the means for emitting a second light emission from within the interpane space of the insulating glass unit comprises a field generator for exciting a gas disposed in the interpane space to form a plasma.

53. The apparatus of claim 52, wherein the generator is configured to generate an oscillating magnetic field proximate an outer surface of the insulating glass unit.

54. The apparatus of claim 43, further including a computer.

55. The apparatus of claim 54, further including a color measuring device configured to generate a first signal to a computer; and
the first signal is based on light sensed by the first photosensor from the first light emission.

56. The apparatus of claim 55, further including a gas fill concentration measuring device configured to provide a second signal to the computer; and
the second signal is based on light sensed by the second photosensor from the second light emission.

57. The apparatus of claim 56, wherein the computer is configured to reject or accept the insulating glass unit based upon both the first signal and the second signal.

58. The apparatus of claim 56, wherein the computer is configured to decide whether to accept the insulating glass unit based upon both the first signal and the second signal.

59. The apparatus of claim 56, wherein the computer is configured to:
compare the first signal with a first acceptable range;
compare the second signal with a second acceptable range; and
generate a reject signal if the first signal is outside the first acceptable range or if the second signal is outside the second acceptable range.

60. The apparatus of claim 56, wherein the computer is configured to:
compare the first signal with a first acceptable range;
compare the second signal with a second acceptable range; and generate an accept signal if the first signal is within the first acceptable range and the second signal is within the second acceptable range.

61. The apparatus of claim 56, wherein the computer is configured to correct the second signal to compensate for a color change occurring in light from the second light emission as that light passes through a single pane of the insulating glass unit.

62. The apparatus of claim 61, wherein the computer is configured to calculate a color change that occurs in light from the first light emission as it passes through at least a portion of the insulating glass unit.

63. The apparatus of claim 62, wherein the computer is configured to compare a known color of light emitted by the first light source with a color of light received by the first photosensor to calculate the color change that occurs in the light from the first light emission as it passes through at least a portion of the insulating glass unit.

* * * * *